(12) United States Patent
Hovland et al.

(10) Patent No.: US 6,169,914 B1
(45) Date of Patent: Jan. 2, 2001

(54) DEVICES AND METHODS FOR MONITORING FEMALE AROUSAL

(75) Inventors: Claire T. Hovland, Minnetonka, MN (US); L. Dean Knoll, Brentwood, TN (US); Jerome H. Abrams; Curtis E. Olson, both of St. Paul, MN (US)

(73) Assignee: Urometrics, Inc., St. Paul, MN (US)

( * ) Notice: Under 35 U.S.C. 154(b), the term of this patent shall be extended for 0 days.

(21) Appl. No.: 09/229,735

(22) Filed: Jan. 13, 1999

Related U.S. Application Data

(60) Provisional application No. 60/071,002, filed on Jan. 13, 1998, provisional application No. 60/071,022, filed on Jan. 13, 1998, and provisional application No. 60/099,036, filed on Sep. 3, 1998.

(51) Int. Cl.$^7$ .................................................. A61B 5/00
(52) U.S. Cl. ..................... 600/340; 600/324; 600/454; 600/459
(58) Field of Search ..................... 600/310, 322, 600/323, 324, 325, 340, 341, 345, 437, 454, 455, 456, 459, 465

(56) References Cited

U.S. PATENT DOCUMENTS

| | | |
|---|---|---|
| 4,224,949 | 9/1980 | Scott et al. . |
| 4,396,019 | 8/1983 | Perry, Jr. . |
| 4,541,439 | 9/1985 | Hon . |
| 4,757,823 | 7/1988 | Hofmeister et al. . |
| 4,827,946 | 5/1989 | Kaali et al. . |
| 4,869,258 | 9/1989 | Hetz . |
| 5,417,207 | 5/1995 | Young et al. . |
| 5,499,631 | 3/1996 | Weiland . |
| 5,565,466 | 10/1996 | Gioco et al. . |
| 5,575,289 | 11/1996 | Skidmore . |
| 5,731,339 | 3/1998 | Lowrey . |
| 5,782,778 | 7/1998 | De Briere et al. . |

FOREIGN PATENT DOCUMENTS

| | | |
|---|---|---|
| 31 40265 | 4/1983 | (DE) . |
| 0 094 749 | 11/1983 | (EP) . |
| WO 96/29927 | 10/1996 | (WO) . |
| WO 98/06333 | 2/1998 | (WO) . |
| WO 98/42255 | 10/1998 | (WO) . |

OTHER PUBLICATIONS

Semmlow, John L., et al., "Sexual Instrumentation," 8088 IEEE Transactions on Biomedical Engineering, vol. BME–30, No. 6, pp. 309–319, Jun. 1983.

Shapiro, Arthur, et al., "Vaginal Blood Flow Changes During Sleep and Sexual Arousal," APSS Meeting, vol. 4, No. 3, p. 394, 1967.

Cohen, Harvey D., et al., "Vaginal Blood Flow During Sleep," APSS Meeting, vol. 7, No. 2, pp. 338, 1970.

Karacan, I., et al., "The Clitoral Erection Cycle During Sleep," APSS Meeting, vol. 7, No. 2, pp. 338, 1970.

(List continued on next page.)

Primary Examiner—Eric F. Winakur
(74) Attorney, Agent, or Firm—Dicke, Billig & Czaja

(57) ABSTRACT

Devices and methods according to embodiments of the invention measure physiological changes that occur in the female during sexual arousal. These include changes in clitoral, vaginal-artery, and/or vaginal-capillary blood flow, clitoral engorgement, and bioimpedance, to name a few. Feedback devices and methods assist a patient or medical professional to determine when arousal occurs and what its best triggers are for a particular patient. Overnight arousal-event monitoring, or other continuous monitoring over extended periods of time, either at home or away from home, allows diagnosis of vasculogenic impairment or other problems. The effects of medicinal therapies aimed at female sexual dysfunction can be quantified and used to titrate proper dosages. Embodiments of the invention provide objective, quantifiable measures of multiple physiological variables associated with female arousal, in a manner heretofore unseen in the prior art.

36 Claims, 11 Drawing Sheets

OTHER PUBLICATIONS

Karacan, I., et al., "The Effect of Sexual Intercourse on Sleep Patterns and Nocturnal Penile Erections," APSS Meeting, vol. 7, No. 2, pp. 338–339, 1970.

Bird, C.G., "Oxygen Tension and Blood Oxygen Content," Anaesthesia, vol. 26, No. 2, pp. 192–198, Apr. 1971.

Geer, Ph.D., James H., et al., "Sexual Arousal in Women: The Development of a Measurement Device for Vaginal Blood Volume," Archives of Sexual Behavior, vol., 3, No. 6, pp. 559–564, 1974.

Frank, E., et al., "Frequency of Sexual Dysfunction in 'Normal' Couples," New England Journal of Medicine, 299:111–115, 1978.

Beck, Gayle J., "Operating Characteristics of the Vaginal Photoplethysmograph: Some Implications for its Use," Archives of Sexual Behavior, vol. 12, No. 1, pp. 43–58, 1983.

Sintchak, George, "A Vaginal Plethysmograph System," Psychophysiology, vol. 12, No. 1, pp. 113–117, 1975.

Geer, James H., "Direct Measurement of Genital Responding," American Psychologist, pp. 415–418, Mar. 1975.

Stern, M.D., "In Vivo Evaluation of Microcirculation by Coherent Light Scattering," Nature, vol. 254, pp. 56–58, Mar. 1975.

Tahmoush, Albert J., et al., "Characteristics of a Light Emitting Diode—Transistor Photoplethysmograph," Psychophysiology, vol. 13, No. 4, pp. 357–362, Feb. 1976.

Hoon, Peter W., et al., "Physiological Assessment of Sexual Arousal in Women," Psychophysiology, vol. 13, No. 3, pp. 196–204, May 1976.

Geer, Ph.D., James H., et al., "Vaginal Blood Volume Responses During Masturbation," Archives of Sexual Behavior, vol. 5, No. 5, pp. 403–413, 1976.

Wincze, Ph.D., John P., et al., "Sexual Arousal in Women: A Comparison of Cognitive and Physiological Responses by Continuous Measurement," Archives of Sexual Behavior, vol. 6, No. 2, pp. 121–133, 1977.

Sarrel, M.D., P.M., et al., "Investigation of Human Sexual Response Using a Cassette Recorder," Archives of Sexual Behavior, vol. 6, No. 4, pp. 341–348, 1977.

Levin, R.J., et al., "Haemodynamic Changes of the Human Vagina During Sexual Arousal Assessed by a Heated Oxygen Electrode," Proceedings of the Physiological Society, pp. 23–24, Nov. 1977.

Wagner, M.D., Gorm, et al., "Oxygen Tension of the Vaginal Surface During Sexual Stimulation in the Human," Fertility and Sterility, vol. 30, No. 1, pp. 50–53, Jul. 1978.

Abel, M.D., Gene G., et al., "Women's Vaginal Responses During REM Sleep," Journal of Sex & Marital Therapy, vol. 5, No. 1, pp. 5–14, 1979.

Hoon, Peter W., "The Assessment of Sexual Arousal in Women," Progress in Behavior Modification, vol. 7, pp. 1–61, 1979.

Henson, Claudia, et al., "Women's Sexual Arousal Concurrently Assessed by Three Genital Measures," Archives of Sexual Behavior, vol. 8, No. 6, pp. 459–469, 1979.

Hatch, Ph.D., John P., "Vaginal Photoplethysmography: Methodological Considerations," Archives of Sexual Behavior, vol., 8, No. 4, pp. 357–374, 1979.

Levin, R.J., et al., "Sexual Arousal in Women—Which Haemodynamic Measure Gives the Best Assessment?" Proceedings of the Physiological Society, pp. 22–23, Jan. 1980.

Wagner, M.D., Gorm, et al., "Vaginal Blood Flow During Sexual Stimulation," Obstetrics & Gynecology, vol. 56, No. 5, pp. 621–624, Nov. 1980.

Henson, Ph.D., Donald, E., et al., "Labial and Vaginal Blood Volume Responses to Visual and Tactile Stimuli," Archives of Sexual Behavior, vol. 11, No. 1, pp. 23–31, 1982.

Semmens, M.D., James P., et al., "Estrogen Deprivation and Vaginal Function in Postmenopausal Women," Journal of the American Medical Association, vol. 248, No. 4, pp. 445–448, Jul. 1982.

Hoon, Ph.D., Peter W., "Physiologic Assessment of Sexual Response in Women: The Unfulfilled Promise," Clinical Obstetrics and Gynecology, vol. 27, No. 3, pp. 767–780, Sep. 1984.

Hoon, Peter W., et al., "Infrared Vaginal Photoplethysmography: Construction, Calibration, and Sources of Artifact," Behavioral Assessment, vol. 6, pp. 141–152, 1984.

Wagner, M.D., G., et al., "Diaphragm Insertion Increases Human Vaginal Oxygen Tension," American Journal of Obstetrics and Gynecology, vol. 158, No. 5, pp. 1040–1043, May 1988.

Sarrel, M.D., Philip M., "Sexuality and Menopause," Obstetrics & Gynecology, vol. 75, No. 4 (Supplement), pp. 26–30, Apr. 1990.

Levin, R.J., "VIP, Vagina, Clitoral and Periurethral Glans— An Update on Human Female Genital Arousal," Exp. Clin. Endocrinol., vol. 98, No. 2, pp. 61–69, 1991.

Nonin™ "8800 Cardiorespiratory Oximeter" brochure, 1991.

Nonin™ "The Most Versatile Pulse Oximeter" brochure, 1993.

Nonin™ "8600 Portable Pulse Oximeter—Reliable Information at a Glance" brochure, 1993.

Meuwissen, Ph.D., Ingrid, et al., "Female Sexual Arousal and the Law of Initial Value: Assessment at Several Phases of the Menstrual Cycle," Archives of Sexual Behavior, vol. 22, No. 5, pp. 403–413, 1993.

Wincze, Ph.D., John P., et al., "Sexual Arousal in Diabetic Females: Physiological and Self–Report Measures," Archives of Sexual Behavior, vol. 22, No. 6, pp. 587–601, 1993.

Schabauer, M.D., Alexander M.A., et al., "Cutaneous Laser Doppler Flowmetry: Applications and Findings," Mayo Clin. Proc., vol. 69, pp. 564–574, Jun. 1994.

Laan, Ellen, et al., "Assessment of Female Sexual Arousal: Response Specificity and Construct Validity," Psychophysiology, vol. 32, pp. 476–485, 1995.

Park, K., et al., "Vasculogenic Female Sexual Dysfunction: The Hemodynamic Basis for Vaginal Engorgement Insufficiency and Clitoral Erectile Insufficiency," International Journal of Impotence Research, vol. 9, pp. 27–37, 1997.

Burnett, Arthur L. et al., "Immunohistochemical Description of Nitric Oxide Synthase Isoforms in Human Clitoris," Journal of Urology, vol. 158, pp. 75–78, Jul. 1997.

Sarrel, P.M., "Ovarian Hormones and Vaginal Blood Flow: Using Laser Doppler Velocimetry to Measure Effects in a Clinical Trial of Post–Menopausal Women," International Journal of Impotence Research, vol. 10, Supplement 2, pp. 91–93, 1998.

Goldstein, I., "Vasculogenic Female Sexual Dysfunction: Vaginal Engorgement and Clitoral Erectile Insufficiency Syndromes, "International Journal of Impotence Research, vol. 10, Supplement 2, pp. 84–90, 1998.

Levin, R.J., "Sex and the Human Female Reproductive Tract—What Really Happens During and After Coitus," International Journal of Impotence Research, vol. 10, Supplement 1, pp. 14–21, 1998.

Lann, E. et al., "Physiological Measures of Vaginal Vasocongestion," International Journal of Impotence Research, vol. 10, Supplement 2, pp. 107–110, 1998.

No Author, "Psychology and Life Periods of Women," Obstetrics and Gynecology, Ch. 4, pp. 50–59, Undated.

No Author, "Sexual Responses of Women, Dysmenorrhea, and Premenstrual Tension," Obstetrics and Gynecology, Ch. 8, pp. 97–108, Undated.

Nonin™ "Instruction and Service Manual, Models 8500 and 8500M, Hand Held Pulse Oximeters," pp. 28–37, Undated.

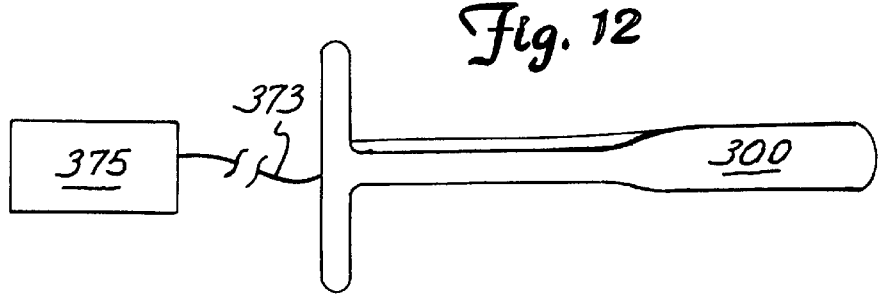
Fig. 12
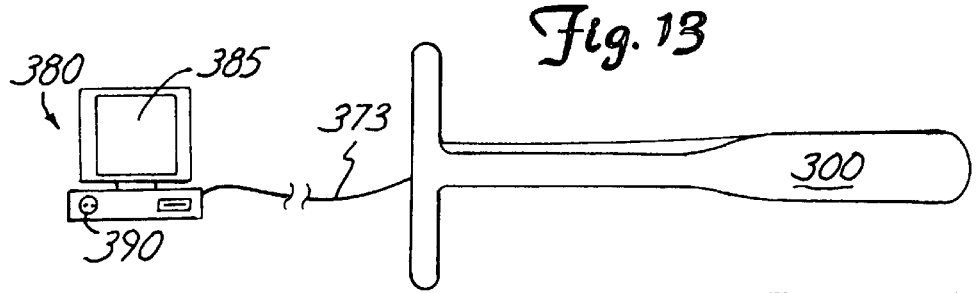
Fig. 13
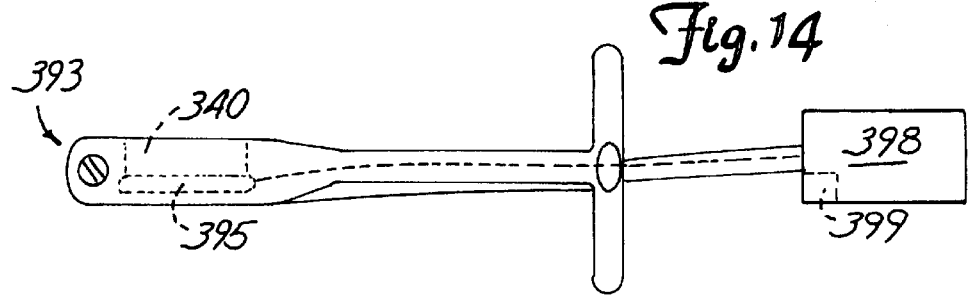
Fig. 14
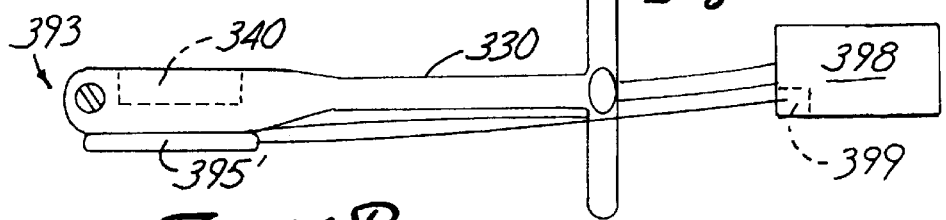
Fig. 14A
Fig. 14B

DEVICES AND METHODS FOR MONITORING FEMALE AROUSAL

CROSS-REFERENCE TO RELATED APPLICATIONS

The subject matter of this application is related to the subject matter of commonly assigned co-pending U.S. patent application Ser. No. 60/071,002, filed Jan. 13, 1998, Ser. No. 60/071,022, filed Jan. 13, 1998, and Ser. No. 60/099,036, filed Sep. 3, 1998, priority to all of which is claimed under 35 U.S.C. § 119(e) and all of which are incorporated herein by reference.

BACKGROUND OF THE INVENTION

Until recently, most vasculogenic sexual-dysfunction research has focussed on males, e.g. on physiologic causes of erectile insufficiency. Abnormal reduction of blood flow through the penile cavernosal arteries and excess venous outflow, i.e. veno-occlusive dysfunction, are well-recognized physiologic causes of impotence and have been the subject of intense study. Now, however, an increasing amount of research is being conducted in the field of vasculogenic female sexual dysfunction.

Studies of sexual dysfunction in couples have revealed that more females than males may experience arousal or orgasmic problems. Whereas 40% of men experienced erectile or ejaculatory dysfunction in one such study, arousal or orgasmic dysfunctions affected 63% of women. See Frank, E., et al., "Frequency of sexual dysfunction in 'normal' couples," *N Engl J Med* 1978; 299: 111–115, which is incorporated herein by reference. Vasculogenic factors are thought to be one of the primary causes of female sexual dysfunction, and increasing age and the onset of menopause contribute to the problem.

It is known that during normal sexual function, the female undergoes many physiological changes. These changes include, among others, increased labial flow, dilation of the introitus, changes in vaginal-wall blood flow (resulting in color change, for example), vaginal lubrication (transudates), vaginal dilation, vaginal lengthening, nipple and clitoral erections, muscle contractions, pupil dilation, increased blood pressure and heart rate, and skin blushing.

Because the prior art has focused primarily on erectile insufficiency in males and other male-related problems, there have been relatively few attempts to effectively determine and treat causes of female sexual dysfunction, for example by monitoring or measuring the above-referenced physiological changes that the female under goes during sexual arousal.

Ultrasound Devices

Recent research indicates that organic female sexual dysfunction may be related in part to vasculogenic impairment of the hypogastric-vaginal/clitoral arterial bed. Ultrasound testing and monitoring of New Zealand White female rabbits has caused several researchers to conclude that vaginal engorgement and clitoral erection depend on increased blood flow, and that certain organic disease states may reduce such flow. Atherosclerosis is thought to be associated with vaginal engorgement insufficiency and clitoral erectile insufficiency. See K. Park, I. Goldstein, et al., "Vasculogenic female sexual dysfunction: The hemodynamic basis for vaginal engorgement insufficiency and clitoral erectile insufficiency," *Intl J Impotence Res* 1997; 9:27–37, which is incorporated herein by reference. The Park article reported use of an electrode for pelvic nerve stimulation, and reported use of laser Doppler ultrasound for blood flow measurements in cavernosal arteries in the clitoris and vaginal walls of rabbits.

The Park article based its conclusions strictly on an animal model. To obtain blood flow measurements in the experimental rabbits, incisions were made and laser Doppler flow probes were placed directly into the vaginal muscularis layer and into the clitoral corporal bodies. Incisions were necessary because generally speaking, the laser energy generated by such probes does not penetrate tissue to an extent sufficient to measure arterial blood flow. Although the article theorized that duplex Doppler investigations might be included in future studies with human subjects, it did not address how such investigations would be conducted or what equipment would be acceptable for doing so. Clearly, the invasive devices and strategies applied in Park's animal model are unacceptable for routine use in humans.

Other researchers have used laser Doppler velocimetry to measure vaginal blood flow in human subjects. Dr. P. M. Sarrel of Yale University measured vaginal blood flow using a laser disc probe fitted into a plastic vaginal speculum. The probe emitted monochromatic light for penetrating the skin or mucosal surface of the vagina to a depth of about 1 mm. Cutaneous capillary and arteriolar flow in response to hormone therapy was measured. The speculum was inserted to a controlled depth, specifically a depth of about 6.0 cm, for sampling from the part of the vagina most reflective of hormonal stimulation. See Sarrel, P. M., Dr., "Ovarian hormones and vaginal blood flow: using laser Doppler velocimetry to measure effects in a clinical trial of post-menopausal women," *Intl J Impotence Res,* 1998, 10, Suppl 2, S91–S93. As indicated, the Sarrel article measured the effect of hormone therapy on capillary and arteriolar flow, without considering measurement of arterial flow before, during or after a period of active sexual arousal. Further, it is unclear from the article exactly how the laser disc probe and speculum are attached or disposed with respect to each other.

U.S. Pat. Nos. 5,565,466 and 5,731,339 to Gioco, et al. and Lowrey, respectively, briefly reference use of Doppler ultrasonic velocimetry to measure blood flow in connection with modulation of the female sexual response. It is unclear how exactly this measurement is accomplished, however. U.S. Pat. No. 4,541,439 to Hon discloses a device for monitoring capillary blood flow. The device must be placed between the vaginal and cervical walls, and then an expandable bladder inflated to create a tight fit. U.S. Pat. No. 4,757,823 to Hofmeister discloses a device for monitoring uterine blood flow, the device including a cervical cup that must be shaped and sized to closely fit the woman's cervix. U.S. Pat. Nos. 5,499,631 and 4,224,949 to Weiland and Scott, et al., respectively, disclose vaginal probes for detection of estrus in bovine.

Finally, handheld ultrasound measurement devices are common in the art for measuring blood flow in connection with e.g. cardiac output. U.S. Pat. No. 5,575,289 to Skidmore, for example, discloses such a device for measuring cross-sectional area and blood-flow velocity in a cardiac-output context.

An important limitation with handheld ultrasound devices is that the angle of incidence, i.e. the angle between the ultrasonic beam direction and the blood-flow vector, can vary unacceptably from reading to reading over time, or even during a single reading. This variability is a result of the instability and imprecision inherent in a handheld device. The medical professional does not know what the angle of incidence is, and, even if a desired angle is known, achieving that desired angle reproducibly on repeat measurements is very difficult during a diagnostic procedure that requires many separate measurements. Even if the relevant calculations eliminate the need to know the precise angle, e.g. by taking velocity ratios to effectively eliminate the angle variable, the angle must be held constant. This instability represents a significant disadvantage with previous ultrasound devices.

The importance of maintaining fixed angle of incidence in monitoring e.g. blood flow in the male genital region is disclosed in commonly assigned PCT Publication No. WO 98/06333, which is incorporated herein by reference. This publication focuses more on the male anatomy than the female anatomy, however.

Vaginal Photoplethysmography

One of the physiological changes that occurs during female sexual arousal is an increase in vaginal-wall blood flow, as referenced above. Vaginal wall capillary blood flow changes have been measured by photoplethysmography. A light emitter, e.g. a laser or infrared diode, generates a light that is reflected by the vaginal wall (or the skin, in non-vaginal applications) to a photodetector. Changes in the intensity of the reflected light are related to vascular changes that occur in the vaginal tissue; the amount of blood in the tissue affects the amount of light that is reflected or "back-scattered" and therefore that reaches the photocell or other optical sensor.

The most common vaginal photoplethysmograph is a tampon-sized device with a diode light source and a light detector, such as a phototransistor. A DC signal from the probe varies as a function of total pooled vaginal blood volume (VBV). An AC signal, on the other hand, varies with vaginal pulse amplitude (VPA), i.e. pulsatile changes in the vaginal capillary bed as a function of each cardiac stroke. The amplitude of the AC signal generated by the photodetector thus is modulated by pulsatile blood flow. During sexual arousal of the female, the increase in blood flow to the vaginal wall creates an increase in the VPA.

Current vaginal photoplethysmography presents a number of unresolved problems, however. It has been unclear, for example, whether the AC component of the signal (representing VPA) or the DC component of the signal (representing VBV) is more sensitive to changes in the vaginal capillaries, i.e. to sexual arousal. Artifacts and other problems with the data due to motion, changes in vaginal pH, changes in sensor characteristics, etc. contribute to the problems with photoplethysmographic methods.

Discussions of photoplethysmographic devices and methods can be found in the Goldstein, et al., article reference above, and in the following articles, all of which are incorporated herein by reference:

Geer, James H., "Direct Measurement of Genital Responding," *American Psychologist,* March, 1975, pp. 415–418;

Henson, et al., "Labial and Vaginal Blood Volume Responses to Visual and Tactile Stimuli," *Archives of Sexual Behavior* 11, No. 1., pp. 23–31, 1982.

Hoon, et al., "Infrared Vaginal Photoplethysmography: Construction, Calibration, and Sources of Artifact," *Behavioral Assessment* 6, pp. 141–152, 1984;

Laan, et al., "Assessment of female sexual arousal: Response specificity and construct validity," *Psychophysiology* 32, pp. 476–485, 1995;

Sintchak, et al., "A Vaginal Plethysmograph System," *Psychophysiology* 12, No. 1, pp. 113–117, 1975;

Tahmoush, et al., "Characteristic of a Light Emitting Diode—Transistor Photoplethysmograph," *Psychophysiology* 13, No. 4, pp. 357–362, 1976;

Pulse Oximetry

Pulse oximetry determines oxygen saturation of hemoglobin in the blood by measuring the color difference between well-oxygenated, bright-red blood and poorly oxygenated, darker-red blood. To the inventors' knowledge, however, pulse-oximetry devices and methods have typcially been developed for transmission through tissue, for example the ear lobe, and have not been applied to the vaginal environment. Further, no known pulse oximetry devices have been especially adapted for use in the vaginal environment.

A typical pulse oximeter shines both red and infrared light through tissue and measures the ratio of absorbed red and infrared light to determine oxygen saturation. It also detects changes in signals caused by arterial blood pressure pulses. Percentage oxygen saturation is then displayed as the variable $SpO_2$, which is calculated by a known mathematical formula. Typical pulse oximeters are available from e.g. Nonin Medical, Inc., Plymouth, Minn., with sensors that attach to e.g. the fingers, toes, or ears, or other areas of the body.

SUMMARY OF THE INVENTION

The prior art fails to address a number of important issues related to the determination of female sexual arousal, alluded to in part above. To overcome the shortcomings of the prior art, devices and methods according to embodiments of the invention measure physiological changes that occur in the female during sexual arousal. These include changes in clitoral, vaginal-artery, and/or vaginal-capillary blood flow, clitoral engorgement, and bioimpedance, to name a few. Feedback devices and methods assist a patient or medical professional to determine when arousal occurs and what its best triggers are for a particular patient. Overnight arousal-event monitoring, or other continuous monitoring over extended periods of time, either at home or away from home, allows diagnosis of vasculogenic impairment or other problems. The effects of medicinal therapies aimed at female sexual dysfunction can be quantified and used to titrate proper dosages. Embodiments of the invention provide objective, quantifiable measures of multiple physiological variables associated with female arousal, in a manner heretofore unseen in the prior art.

Other advantages and features of the embodiments disclosed herein will be apparent from the remainder of the application.

BRIEF DESCRIPTION OF THE DRAWINGS

The invention will be described with reference to the figures, in which like reference numerals denote like elements and in which:

FIGS. 12–13 are schematic diagrams showing connection of the device shown in FIGS. 8–9 with associated electronics;

FIGS. 14–14A show vaginal oximeter devices according to alternative embodiments;

FIG. 14B is a schematic illustration of feedback arrangements according to embodiments of the invention;

DETAILED DESCRIPTION OF PREFERRED EMBODIMENTS

According to embodiments of the invention to be first described, blood-flow velocities in the female cavernosal and/or vaginal arteries are measured and evaluated, e.g. for use in diagnosing and treating female sexual dysfunction.

Ultrasound-Type Devices and Methods

Figure 1:
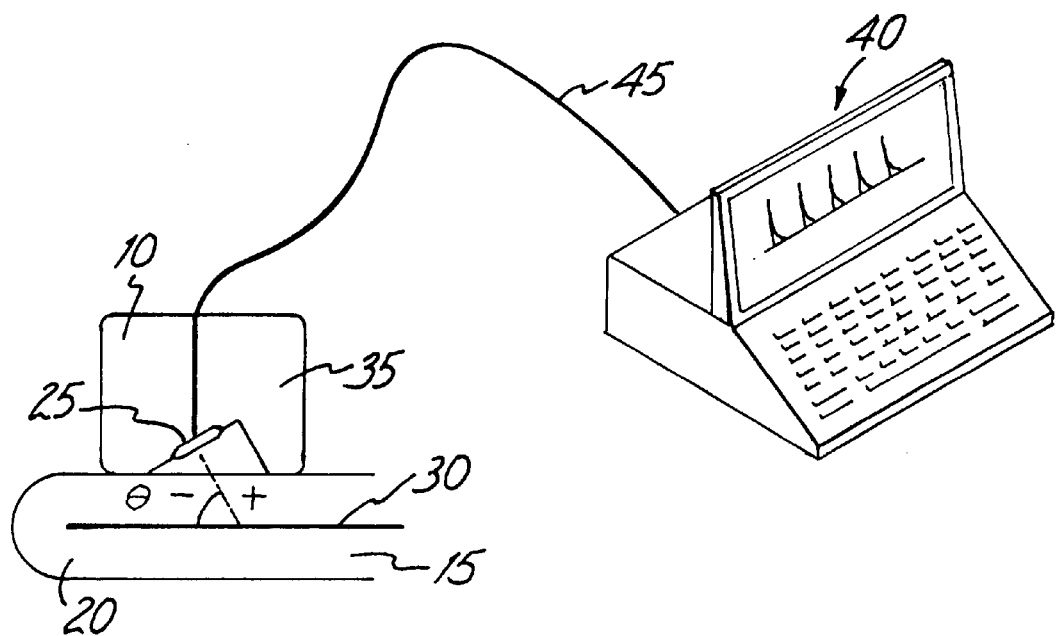
FIG. 1 shows a measurement device for measuring blood-flow velocities in the female cavernosal artery, according to an embodiment of the invention.

As shown in FIG. 1, one probe embodiment 10 measures blood flow in cavernosal artery 15 in the female clitoris 20 by creating a substantially fixed, substantially known angle θ between an ultrasound-type or other transducer 25 and the primary blood flow vector 30 in cavernosal artery 15. Transducer 25 preferably is placed in a housing 35 to substantially fix this angle mechanically and to provide a holding mechanism for transducer placement on or in the region of the clitoris. A securing strap may be used, comprising tape, elastic, VELCRO type hook-and-loop fasteners, etc.

Control electronics 40 preferably are operably coupled to the transducer by lead(s) 45 or other communication mechanisms or devices. The control electronics are used to transmit and receive the ultrasonic signals, and also can be used in analyzing, storing, displaying, and printing e.g. blood-velocity information for the female corpora cavernosa.

To reduce size and weight, the primary function of the control electronics preferably is data collection and storage for later downloading to a computer or other associated device. A control unit that houses the appropriate electronics can be strapped to the leg or other portion of the patient's body, according to one embodiment. More sophisticated processing electronics also can be incorporated directly, although this likely would increase the unit's size, weight, power requirements, etc. Diurnal and nocturnal monitoring/measurements are contemplated.

Figure 1A:
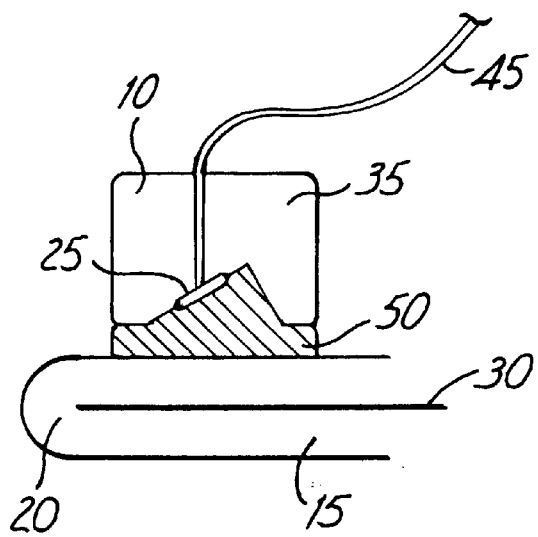
FIG. 1A shows a measurement device used with standoff material.

FIG. 1A shows optional ultrasound standoff 50, preferably made of a material having an ultrasound-transmission velocity similar to that of tissue, to allow the transducer to have less closely focussed optics. The standoff material provides acoustic coupling between the transducer and the clitoris, while maintaining the fixed angle θ between the ultrasound beam and the cavernosal artery. Given the small sizes of the clitoris and clitoral cavernosal artery, a standoff is desirable to allow use of a transducer having a relatively large focal distance. In other words, a transducer can be used having an area of narrowest beam width, i.e. the optimal measurement area, spaced from the transducer by e.g. about 1.2 cm or other dimension that is relatively large compared to the clitoris and cavernosal artery. A standoff also is advantageous given that the clitoris often is tucked into the labia and surrounding tissues. The standoff preferably will not change the angle θ in its design, but will allow the transducer to be placed at a greater distance from the blood flow vector. A higher frequency transducer, which allows a smaller focal area at a shorter distance, can be used instead of or in addition to an ultrasound standoff.

Embodiments of the invention optionally can be used to measure blood velocities in the cavernosal arteries, clitoral diameter, cavernosal artery diameter, and other variables. Measurements or estimates of blood volume flow rates may be made if cavernosal artery diameter is known, measured or estimated. A vasodilator may be ingested, injected or topically or otherwise applied for use with this device to provide measurements of velocity(ies) and/or flow(s) in the cavernosal artery or arteries both before and after administration of the drug.

Embodiments of the invention also permit information to be obtained about the luminal patency of the cavernosal arteries in the clitoris. Assessment of luminal patency is believed important in developing a greater understanding of female sexual dysfunction. Additionally, peak systolic and end diastolic velocities have value in understanding arteriogenic and veno-occlusive mechanisms in the male penis. The clitoris is anatomically similar to the male penis and similar functional information is expected to be obtained by blood-velocity measurements in the clitoral cavernosal arteries.

Figure 2:
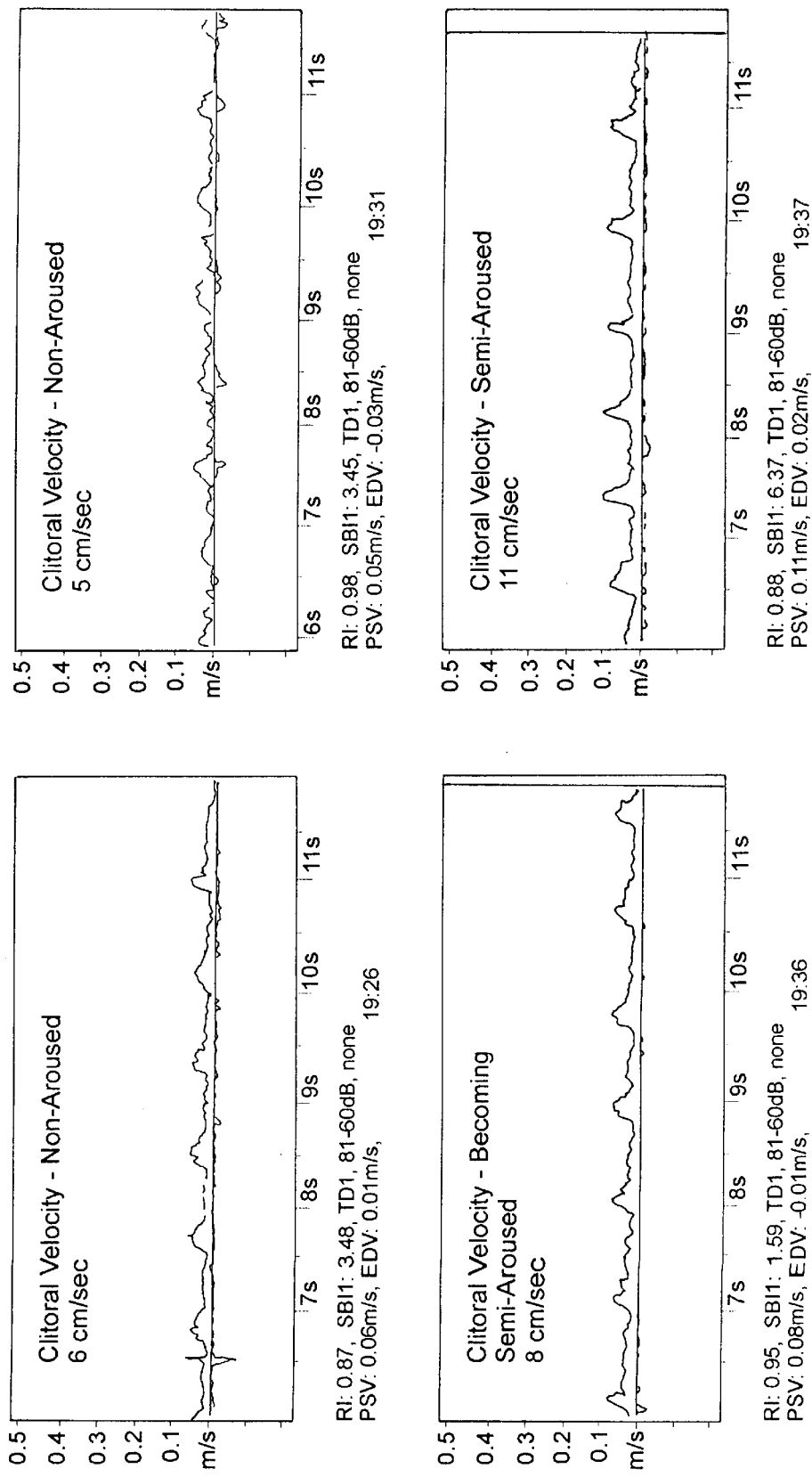
FIGS. 2–3 show plots of blood velocity vs. time in the female clitoris.
Figure 3:
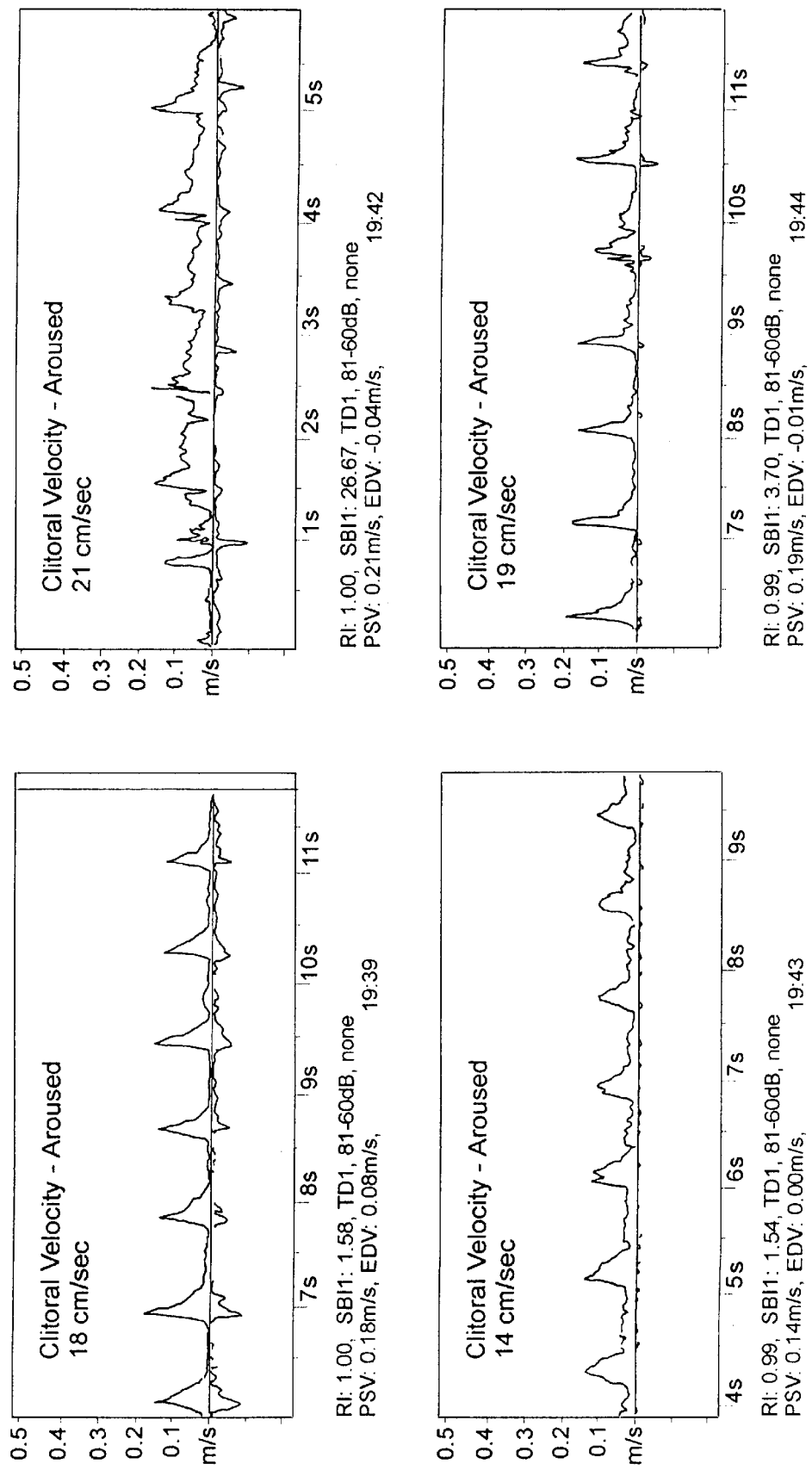

FIGS. 2–3 show plots of clitoral blood velocity in non-aroused, semi-aroused, and aroused states of a healthy human female with no known sexual dysfunction. The upper left plot of FIG. 2, for example, shows a peak systolic velocity of about 6 cm/sec in a non-aroused state. In the lower right plot, taken about 11 minutes later, the subject is semi-aroused and clitoral blood velocity has increased to about 11 cm/sec. In the aroused states depicted in the upper left and lower right plots of FIG. 3, taken respectively at 13 minutes and 18 minutes, clitoral blood velocity has increased to 18 cm/sec and 19 cm/sec. Embodiments of the invention can be used to accurately measure and monitor blood velocities and derive blood-flow rates and other parameters.

Figure 4:
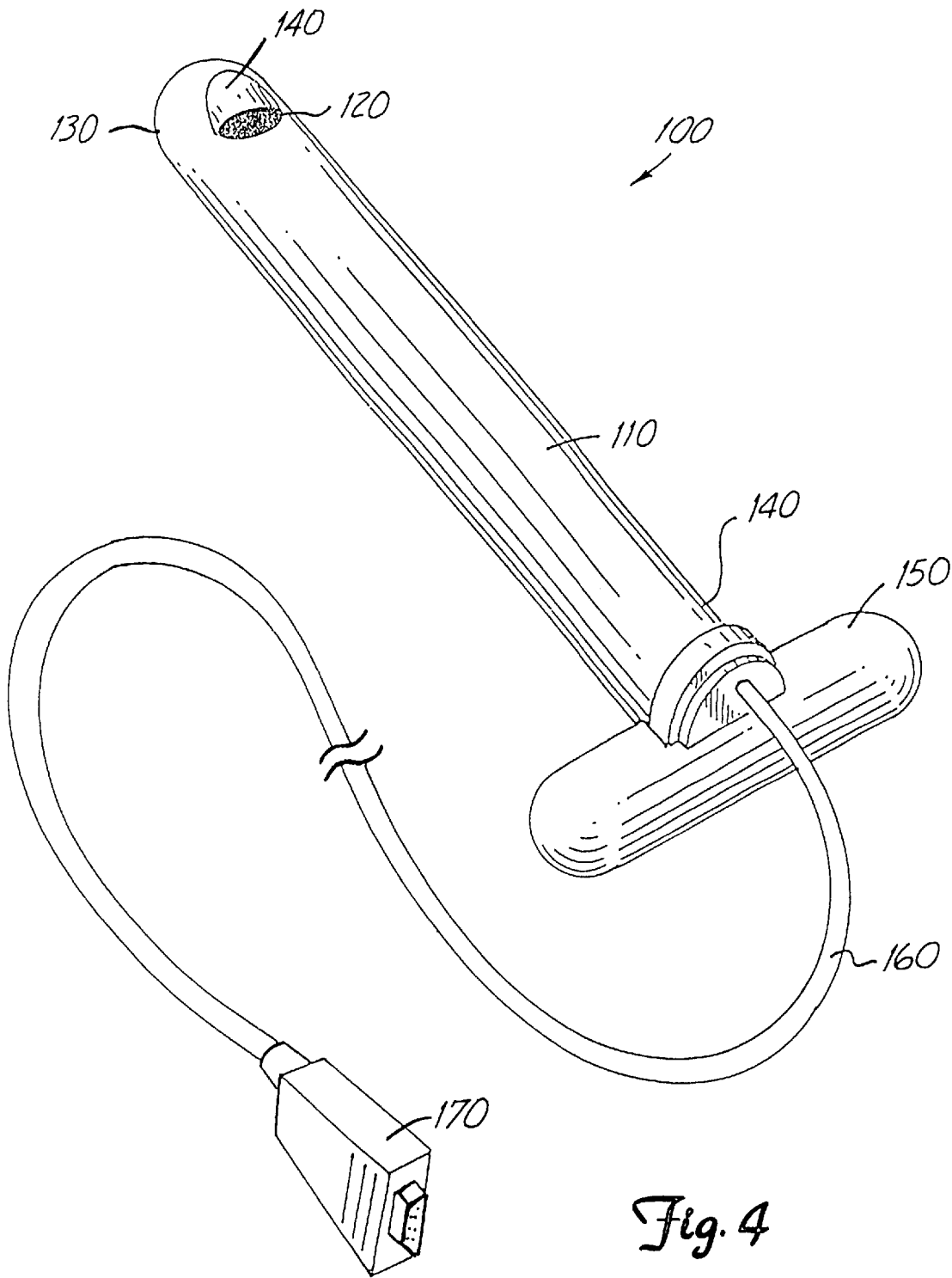
FIG. 4 shows a measurement device for measuring blood-flow velocities in the vaginal arteries, according to an embodiment of the invention.
Figure 5:
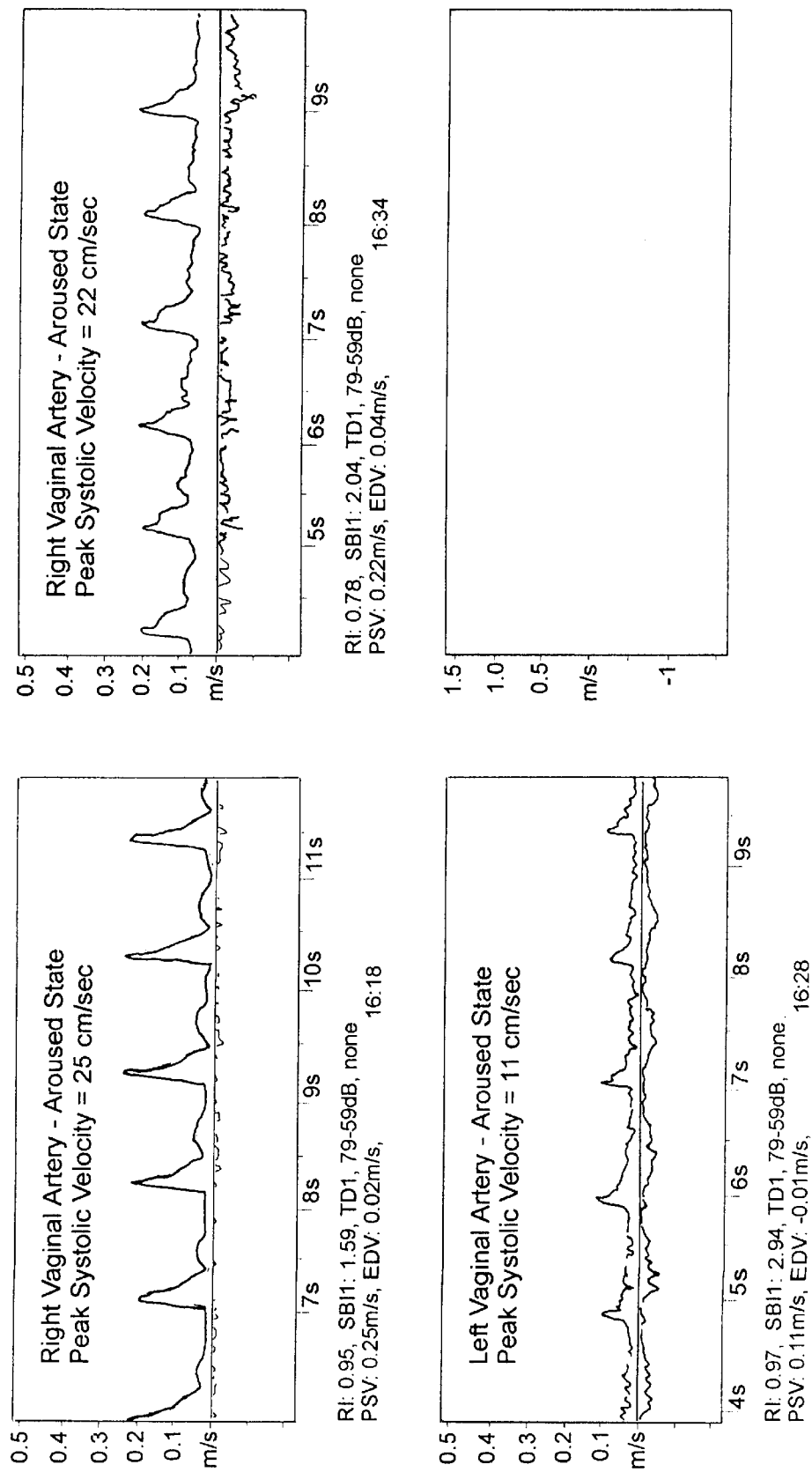
FIG. 5 shows plots of vaginal-artery blood velocity vs. time using a measurement device according to the embodiment of FIG. 4.

Turning to FIGS. 4–5, devices and methods for monitoring e.g. vaginal-artery blood-flow parameters will now be described.

Measuring device 100 includes elongate shaft 110, which supports transducer 120 at a distal end 130 thereof. Distal end 130 preferably defines recessed portion 140, in which transducer 120 is placed. Recessed portion 140 can accommodate gel or similar acoustically conductive material, and should be completely filled therewith to substantially prevent any air pockets or bubbles that potentially block transmission of ultrasound signals. Further, recessed portion 140 is shaped and transducer 120 is angled to achieve a desired angle of incidence with the vaginal artery or other vessel/region to be monitored, as will be described.

According to one embodiment, shaft 110 can be covered with an ultrasound-transmissive, disposable probe cover or sheath, to keep device 100 clean and out of contact with vaginal fluids. A variety of commercially available probe covers are useable, according to embodiments of the invention.

Transducer 120 is preferably a single Doppler ultrasound transducer for transmitting/receiving ultrasound or other suitable energy to detect Doppler shift, e.g. for calculation of blood velocity, blood-vessel cross-sectional area, or other parameters. Single-transducer embodiments are preferred, for example pulse-wave piezoelectric devices in which a transmit mode is followed by a rest mode, and then a reception mode for receiving the reflected energy. The resulting combination of pulses allows the medical professional to precisely set focus depth. Other transducer arrangements, e.g. dual-transducer arrangements described in the above-referenced PCT Publication No. WO 98/06333, are also contemplated. Whatever transducer arrangement is used, the angle of incidence is mechanically defined and substantially fixed with respect to the blood flow direction in the relevant blood vessel or region.

Disposed at proximal end 140 of shaft 110 is handle 150. Handle 150 is designed to enable a medical professional to easily grasp, insert, remove, and turn probe 100 as needed during a particular diagnostic procedure. Further, extending from proximal end 140 is at least one coaxial cable 160 or other signal-transmission device. Connector 170 is used to connect cable 160 to electronics (not shown in FIG. 4, but similar to electronics shown and described with respect to FIGS. 12–13) that direct the transmission and reception of the ultrasound signals and calculate and display Doppler frequency shift, blood velocity measurements, and/or other data. Proximal end 140 can be of reduced diameter, in the manner of the embodiments of FIGS. 18–19, for example, to facilitate insertion into the vagina.

In fact, the electronics can perform a wide variety of desired calculations and display graphical representations of a wide variety of variables, as chosen by the urologist or other medical professional. Control electronics components useable according to the invention can be purchased from a variety of companies. Graphs of velocity versus time for the vaginal artery can be displayed, as will be described with respect to FIG. 5, during the course of the procedure or afterwards. Further, velocity and/or blood-flow displays can be correlated with electrocardiogram and/or pulse oximetry readings/displays to depict variations in blood velocity with respect to heartbeat. Still further, correlation or simultaneous display with clitoral/cavernosal blood-velocity and blood-flow variables, e.g. as discussed above, can also be accomplished.

The displayed graphical information can be presented in a number of different formats on the display screen. For example, a spectral distribution graphical mode displays a gray scale that represents all of the Doppler frequencies. The greater the shift in frequency, the greater the distance from the baseline on the display screen. In a mean frequency mode, the statistical mean of the Doppler frequencies is displayed, for example as a colored line. In the show index mode, pulsatility, resistance, spectral broadening and heart rate values are displayed. The maximum frequency mode displays maximum frequency shift, for example as a colored line. Finally, the mode frequency graphical mode displays the single frequency that occurs most often during a sample, again as a colored line, for example.

The spectral distribution, maximum frequency and mean frequency displays can be used simultaneously to determine signal quality. When adjusting the transducer(s) to measure velocity in the vaginal arteries, a maximum gray-scale (spectral distribution) signal should be displayed. If the signal is of a good quality, the maximum frequency display and the mean frequency display should follow the wave form displayed by the spectral distribution. The mean frequency should be lower than the maximum frequency, and the distance between the two should be relatively constant. Attention is directed to PCT Publication No. 98/06333, referenced above, for additional discussion of these and other related principles.

An angle of incidence of about 60 degrees is preferred. As angle of incidence increases, Doppler shifting effect diminishes, to the point where at 90 degrees, there is zero Doppler shift. As the angle of incidence decreases, on the other hand, the sonographic or other energy must travel through tissue for a greater distance before hitting the intended target area. That travel is highly attenuative, and signal loss ultimately occurs. About 60 degrees has been found to be a preferable angle of incidence to minimize these disadvantages.

In use, according to one embodiment, the medical professional substantially fills recessed portion 140 with gel or other acoustically conductive material. Probe 100 is then inserted into a patient's vagina to a desired depth and rotated to a desired angle for measuring blood-velocity parameters associated with the vaginal arteries. The best depth will vary with the particular patient, of course, but generally speaking a depth of about 6 cm is desired for measuring blood-velocity parameters associated with the vaginal arteries. (Deeper penetration, of e.g. 11 cm, can result in measurement of the uterine artery. Uterine artery blood-flow measurements may or may not be desirable depending on the particular diagnostic procedure.) Probe 100 then can be rotated to e.g. 9 o'clock or 3 o'clock positions to measure one or both of e.g. the left and right vaginal arteries.

The external shape of probe 100 is designed to hold transducer 120 in a substantially constant orientation with respect to the vaginal artery or other blood vessel being monitored, substantially fixing the angle of incidence. Unlike merely hand-stabilized and/or external devices, probe 100 is held in a relatively stable position and orientation within the vagina. This feature provides accurate, reproducible and reliable measurements.

FIG. 5 illustrates three examples of graphical displays that can be generated using probe 100 of FIG. 4. All three displays show vaginal-artery blood-velocity measurements for a female subject in an aroused state. For the upper left plot, probe 100 is turned to a 9 o'clock position to measure the subject's right vaginal artery. A peak systolic blood velocity of about 25 cm/sec is shown, along with an end diastolic velocity of about 2 cm/sec. The upper right plot shows the same artery about 16 minutes later, with peak systolic and end diastolic velocities of about 22 and about 4 cm/sec, respectively. For the lower left plot, probe 100 has been turned to a 3 o'clock position to measure the subject's left vaginal artery. The peak systolic velocity is considerably lower, about 11 cm/sec, even though the arousal level is approximately the same. Thus, embodiments of the invention can be used to accurately measure and display vaginal-artery and blood-flow parameters of an aroused subject, in a manner heretofore believed unknown in the prior art.

According to one example diagnostic protocol, measurement of vaginal-artery parameters can occur before, during, and after administration of a vasodilator. By comparing the generated plots and data to those of normal patients, health or dysfunction can be diagnosed. Further, in a titration scenario, proper dosage of vasodilation or other medication can be determined for a particular patient by monitoring vaginal-artery response to a range of dosages. Vaginal-artery parameters can also be plotted with or otherwise compared to clitoral parameters, if desired, e.g. to determine a particular mode of dysfunction.

Probe 100 preferably is formed of a biocompatible, readily sterilizable material. Both reusable and disposable embodiments are contemplated, the latter preferably with structure allowing easy removal of transducer 120 for reuse. A condom or similar protective covering can be placed over the probe of this and the other embodiments, the covering preferably not being highly attenuative to ultrasound.

Figure 6:
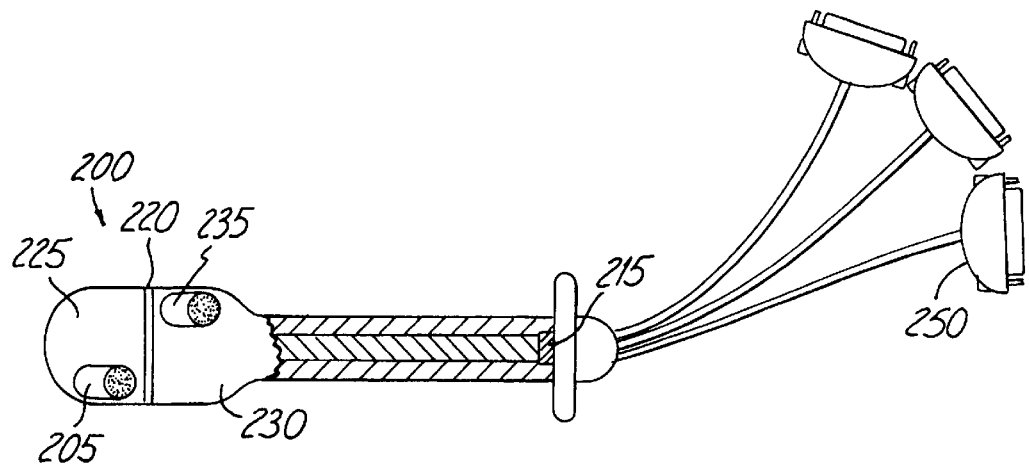
FIGS. 6–7 are top and side views, respectively, showing a measurement device according to an alternative embodiment of the invention.
Figure 7:
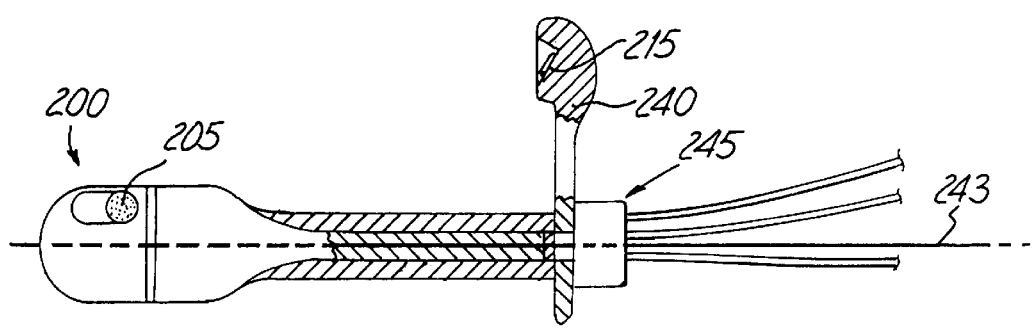
Figure 10:
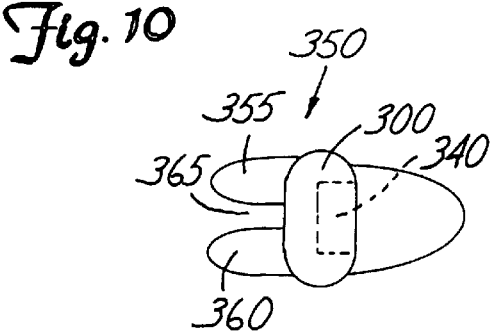
FIGS. 10–11 are end views showing a clip embodiment for use with the oximeter device of FIGS. 8–9.

FIGS. 6–7 show a measurement device according to an alternative embodiment of the invention. This embodiment includes multiple transducers on a single probe, as will be described. The construction of this embodiment allows a patient or medical professional to insert the probe into the vagina with greater precision, e.g. after periods of self stimulation during which the probe is removed.

More specifically, probe 200 includes three fixed-angle transducers 205, 210, 215. Probe 200 also includes transducer housing 220, with two independently rotatable housing sections 225, 230. Housing 220 for transducers 205, 210 allows independent rotational adjustment of each transducer for measurement of blood flow and/or velocities, etc., in both the left and right vaginal arteries. Housing 220 also defines recessed portion 235 for each transducer 205, 210, for a purpose similar to that of recessed portion 140 of the FIG. 4 embodiment.

Probe 200 also includes vertically adjustable housing 240 for supporting transducer 215. Housing 240 can be rotated about the longitudinal axis 243 (FIG. 7) of probe 200 and/or a transverse axis of probe 200, and optionally can be linearly adjusted such that the distance between transducer 215 and the longitudinal axis 243 of probe 200 can be varied. Transducer 215 can be placed in close association with the clitoris of the patient for measurement of blood flow, velocities, etc. in the clitoral cavernosal artery.

Probe 200 further includes adjusting mechanism 245, which has markings for displaying the rotational angles of transducers 205, 210 independently, i.e. the orientation of transducer 205, 210 with respect to transducer 215, and the relative height of transducer 215. Suitable securing mechanisms are contemplated to substantially fix the rotational and/or linear positions of housing sections 225, 230 and housing 240. For example, constrained rubber-type O-rings can be used, which expand to fill the gap between the relatively moving parts of the housing sections or other apparatus. For relatively rotating parts, complementary threads can be used to secure the parts together, with the constrained O-ring in close association therewith.

Probe 200 presents significant advantages, in that simultaneous measurements of the left vaginal artery, right vaginal artery and clitoral cavernosal artery can be taken, displayed and/or stored. Such simultaneous measurement, and associated display and other analysis, allow relatively straightforward, graphical and intuitive correlation between blood-flow parameters for these vessels, in a manner heretofore believed unknown in the prior art.

Further, the substantially fixed, yet readily adjustable, orientation of transducers 205, 210, 215 allows e.g. a medical professional easily and accurately to configure probe 200 in accordance with a particular patient's anatomy. The substantially orthogonal orientation of housing 240 with respect to the remainder of probe 200 allows repeated insertion of probe 200 to a particular depth. Moreover, by substantially aligning transducer 215 with the clitoris upon reinsertion, the overall angular orientation of transducers 205, 210 with respect to the vaginal arteries is achieved and maintained. Thus, after initial configuration by a medical professional, the device can be easily inserted by the patient in the privacy of her place of residence, for example, during periods of stimulation (e.g. vasodilator-induced stimulation, self stimulation, etc.). Probe 200 can include an associated switch, push button or similar actuation device, allowing the patient to start and stop the measurement process easily. Measurements can be stored in an associated memory device operably associated with the transducers via connectors 250, for example. The stored data can be downloaded or otherwise transferred to e.g. appropriate control electronics, for e.g. display and analysis.

Pulse Oximeter Devices and Methods

FIGS. 8–13 show pulse oximeter devices, according to embodiments of the invention, constructed for measuring oxygenation levels of the capillaries in the vaginal wall as a measure of sexual arousal. Unlike photoplethysmographic methods known in the prior art, oximetry methods according to embodiments of the invention determine vaginal-wall hemoglobin oxygenation levels by using a mathematical formula akin to the following:

$$SpO_2 = f\left[\frac{\ln\left(\frac{\min}{\max}\right)_{red}}{\ln\left(\frac{\min}{\max}\right)_{infrared}}\right]$$

By taking a ratio of the variables associated with the minimum and maximum light intensity for e.g. red and infrared light, oximetry methods according to embodiments of the invention eliminate the typical data-reading problems caused with e.g. sensor drift, changing vaginal pH levels and other aberrations. For the first time, the inventors have discovered that using oximetry devices and methods in the vaginal environment solves many of the problems typically associated with the vaginal plethysmographic methods of the prior art.

Oximeter device 300 includes a housing of either one-piece or multiple-piece construction. In the illustrated embodiment, device 300 includes two substantially identical halves 305, 310, preferably held together, at least partially, by recessed screw 315 or equivalent fastener.

The housing of device 300 includes probe-supporting portion 320, taper 325, and neck 330, according to the illustrated embodiment. Of course, a wide variety of housing shapes are contemplated and are useable according to the invention. Probe-supporting portion 320 includes recessed area 335 (FIG. 9) for accommodating oximeter probe 340, as shown. Recess 335 may be the same height as probe 340, to provide a flush mounting arrangement at the surface of probe-supporting portion 320, or may be thicker or thinner than probe 340, to suit the characteristics of a particular patient and/or diagnostic/measurement protocol. Similarly, device 300 may be dimensioned appropriately. According to one specific embodiment, the approximate center of probe 340 is located about 6 cm from the far end of neck 330. Probe 340 itself, according to one embodiment, is about 0.5 cm thick, about 1.5 cm long and about 0.9 cm wide. Of course, a wide variety of dimensions, shapes and materials are contemplated according to the invention.

At the far end of neck 330 relative to probe 340, a clip 350 preferably is provided. Clip 350 serves at least two purposes: first, it assists in holding halves 305, 310 of the housing together, where two-piece embodiments of the housing are used. Second, it can also serve as an insertion-limiting device, enabling the patient or medical professional to know when device 300 has been inserted into the vagina to the proper depth, for accurate positioning of probe 340. (Generally speaking, the outer third of the vagina is more highly vascularized than the remaining, inner two-thirds.)

Clip 350 can be affixed to neck 330 along various points along its length, depending on the desired insertion depth for a particular patient or on the desired diagnostic procedure. Clip 350 preferably is formed of DELRIN or other suitable material.

According to the illustrated embodiment, clip 350 includes legs 355, 360, defining slot 365. End portion 370 (FIG. 11) of neck 330 preferably is formed with a tapered shape, as shown, for easy insertion into and locking within slot 365 of clip 350. Inserting and securing end portion 370 within slot 365 aids in securing housing portions 305, 310 together, along with screw 315 or other fastener. End portion 370, legs 355, 360 and slot 365 preferably are configured such that end portion 370 can be inserted into slot 365 in only one direction, to ensure proper disposition of clip 350 with respect to the remainder of oximeter device 300.

Figure 8:
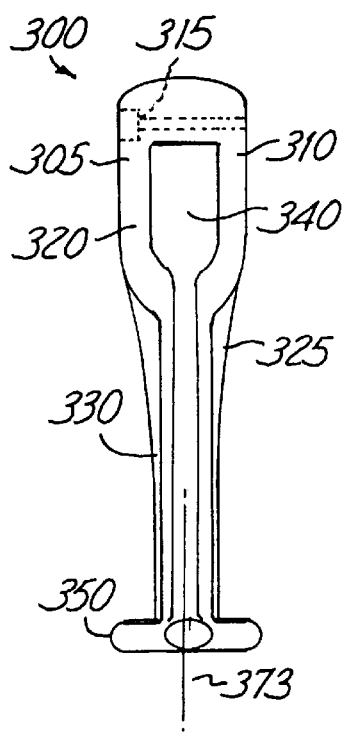
FIG. 8 is a plan view of a vaginal oximeter device according to an embodiment of the invention.
Figure 9:
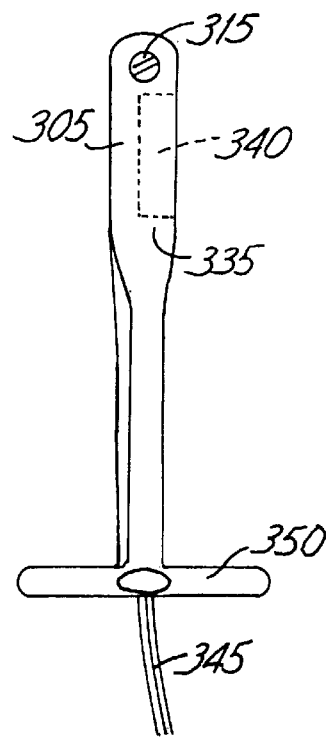
FIG. 9 is a side view of the FIG. 8 vaginal oximeter device.
Figure 11:
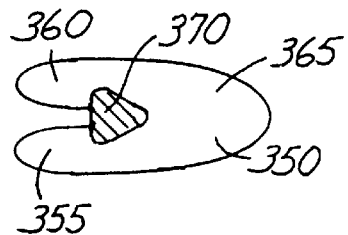

As shown in FIGS. 8 and 12–13, oximeter device 300 is connected by e.g. cable 373 to associated electronics. The FIG. 12 embodiment includes electronics 375, which can include data-processing and/or storage devices for receiving data from probe 340. Control electronics 375 can include devices and configurations shown in commonly assigned PCT International Publication No. WO 98/42255, which is incorporated herein by reference. Further, control electronics 375 can be disposed within a modular box or other housing. At least portions of control electronics 375 can be included in a PC card and/or associated circuitry, a microcard, or other similar substantially modular, readily interchangeable computing technologies.

Given the small sizes associated with these technologies, the housing for control electronics 375 can be of greatly reduced size, for example credit-card size or even smaller. These small sizes are especially useful to reduce the invasiveness and cumbersome nature of electronics typically associated with medical data-gathering devices of this nature. Control electronics 375 can download data to other, more sophisticated computing electronics, for example via hard wiring, a plug-in connection, telephone line, etc., either simultaneously with the monitoring process or after the data has been stored in memory. Further, in addition to or instead of cable 373, embodiments of the invention can include other data-transmission modes, e.g. infrared, fiber optic, wireless, etc.

As shown in FIG. 13, control electronics usable according to the invention also can include computer 380 with display 385 and speaker 390, among other components. Computer 380 can be hard-wired or otherwise connected to oximeter device 300, for example in the manner described immediately above. Further, control electronics 375 of FIG. 12 can download data to a computer 380 in the manner previously described.

In operation, oximeter device 300 is inserted to a desired depth in the vagina and, if desired, turned to a preferred angle. Control electronics 375, computer 380 or another suitable device activates oximeter probe 340 to begin the data-reading process. Oximeter probe 340 records data relating e.g. to pulse and $SpO_2$, for simultaneous or subsequent display/storage. Ultimately, such variables can be displayed with the VPA and VBV information determined e.g. with the photoplethysmographic techniques previously described.

Turning to FIG. 14, oximeter device 393 of this embodiment is substantially similar to previously described oximeter devices 300, but additionally includes, below oximeter probe 340, constant-pressure balloon 395. Balloon 395 is fluidly connected to an appropriate pressure source 398, for example via tubing or other structure defined within or by neck 330. Pressure source 398 can be electrically or manually activated, according to embodiments of the invention. FIG. 14A illustrates alternative balloon placement, in which pressure balloon 395' is disposed on an external surface of the housing for directly contacting the vaginal wall.

With oximeter probes according to the invention, producing acceptable data readings generally requires urging probe 340 against the vaginal wall with just the right amount of contact pressure. Too much contact pressure blocks capillary flow, adversely affecting the data. Too little contact pressure, on the other hand, results in inadequate data readings as well. Additionally, motion artifacts induced by patient movement, the changing size of the vagina as it dilates, and other causes can also create problems with the data. Therefore, to address these problems, pressure balloon 395 or 395' is inflated, under either electronic or manual control, to urge probe 340 against the vaginal wall with a desired contact pressure. The balloon can include pressure transducer 399 operably associated therewith, either at source 398, as shown, or in closer physical association with the balloon, to record internal balloon pressure for correlation to contact pressure in a feedback loop. Electronic pressure control then can be used to automatically maintain a substantially constant contact pressure, despite motion and other potential artifact-inducing events. The above-referenced PCT Publication No. WO 98/06333 provides a discussion of a constant-pressure balloon mechanism that potentially can be applied to the current invention.

Oximeter devices according to the invention provide quantifiable, objective data regarding e.g. vaginal blood flow in a highly effective manner, unknown in the prior art.

Audio and/or Visual Feedback Embodiments

According to alternative embodiments of the invention, audio, visual and/or other feedback tied to e.g. vaginal pulse amplitude (VPA) is used to provide instant feedback to a patient and/or medical professional, feedback that correlates directly and immediately to the state of arousal. FIG. 14B schematically shows a device for monitoring VPA (or another physiological parameter) in operable connection with a feedback device as will be described. As previously discussed, the AC component of the signal from a vaginal photoplethysmograph varies as a function of VPA. During sexual arousal of the female, the increase in blood flow to the vaginal wall creates an increase in the VPA.

According to one embodiment of the invention, a preferably small and unobtrusive device generates an audible sound that increases in intensity, frequency, volume and/or amplitude as VPA increases, i.e. as sexual arousal of the female patient progresses. The sound types can be selected by the medical professional or patient, according to one embodiment, and/or can include a "whoosh" sound to represent fluid flow, a human voice, or other desired sound. A low- or no-signal condition can be represented by a discontinuous, steady or other tone indicating a low or non-existent state of arousal, or an abnormality in reading or obtaining a signal from the sensor. A speaker arrangement, such as is shown in FIG. 13 in connection with a computer, for example, plays the appropriate sounds for the patient directly. Alternatively, other audio feedback devices can also be used.

Instead of or in addition to audio feedback, visual indicators can be used according to the invention. These can include a display with changing colors, a graphical indicator showing pulse amplitude or a correlated variable, an animation, and/or another indicator optionally selectable by the patient. Tactile feedback devices can also (alternatively or additionally) be used, increasing in e.g. temperature and/or frequency of vibration as arousal level increases.

Feedback embodiments of the invention are especially useful with female patients who have decreased sensory perception in the vaginal area or otherwise have trouble recognizing or articulating the relative level of arousal they are experiencing. Feedback device embodiments can be used as a monitoring aid by the patient's gynecologist, psychiatrist or other medical professional, as well as a training aid for the patient and the patient's partner. The objective feedback provided by these embodiments enables the patient to more accurately discern what her level of arousal is and what aspects of touch or other stimulation are the most effective in producing arousal. This eliminates much of the uncertainty and unreliability inherent with self-reporting and other subjective measures.

Feedback embodiments of the invention can be used not only with photoplethysmography devices, but also with oximetry, ultrasound, and other monitoring devices described in this application, for example the "pacifier-type" embodiments described below. In each case, the level of arousal objectively determined by the device is correlated to an audible, visual, tactile and/or other perceivable indicator that is played, broadcast, displayed or otherwise indicated to the patient and/or another party.

Finally, feedback embodiments of the invention are applicable not only to monitoring of vaginal blood flow, but also to e.g. clitoral or nipple engorgement/erection, dilation of the introitus or vaginal, increased labial and/or vaginal flow, changing pH, muscle contraction, or the other physiological changes associated with arousal, such as are discussed earlier.

Bioimpedance-Electrode Embodiments

Figure 15:
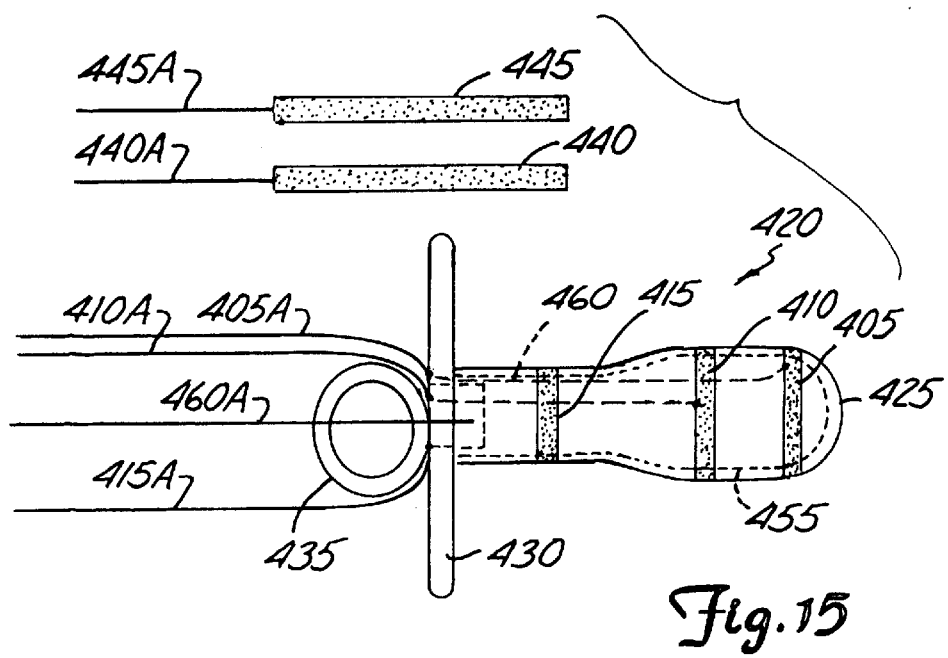
FIG. 15 shows a vaginal bioimpedance measurement device according to an embodiment of the invention.
Figure 16:
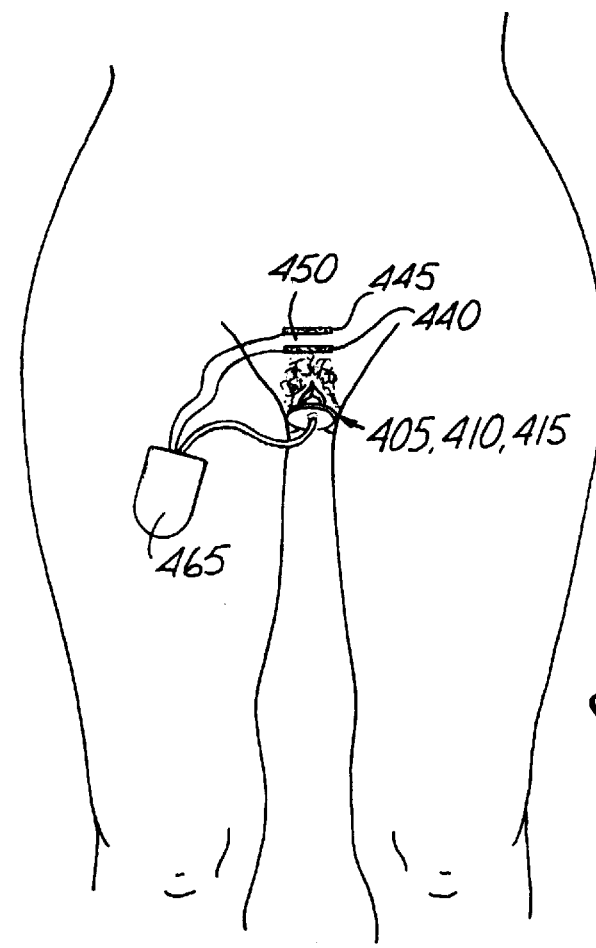
FIG. 16 shows the FIG. 15 device in an in-use position.

According to the embodiments of the invention shown in FIGS. 15–16, volumetric changes in the female vaginal wall, the labia, and/or the clitoris are monitored and evaluated for use in diagnosing vasculogenic causes of female sexual dysfunction.

As shown in FIG. 15, measurement device 400 according to one embodiment includes five bioimpedance electrodes, also called contact or measurement elements. Three of the electrodes, numbered 405, 410 and 415 in FIG. 15, are mounted on an insertion unit 420 that is "pacifier-shaped" and includes tip 425 for insertion into the vagina, base member 430, and handle 435 to facilitate insertion and removal. According to one embodiment, electrode 405 preferably functions as a current injector, and electrodes 410 and 415, which preferably have a substantially fixed separation distance, measure impedance changes in the vagina and provide information regarding e.g. the engorgement of the vaginal wall.

Electrodes 440, 445 preferably are positioned off insertion unit 420 and can be secured to the patient's body, e.g. subumbilically or in another desired position preferably above the pubic hair, as shown in FIG. 16. According to one embodiment, electrodes 415, 440 measure impedance changes across the clitoris, and electrode 445 functions as a current sink. Electrodes 440, 445 optionally are secured to an adhesive strip 450 for substantially fixed positioning relative to each other and easy application to the body.

In one preferred mode of operation, a substantially constant current is passed from electrode 405 to electrode 445. Voltage drop is measured between electrodes 410 and 415, which gives impedance through the equation V=IR, where I is constant. Voltage-drop change between these electrodes primarily will be due to vaginal wall engorgement related to blood-volume increases and decreases. Voltage drop is also measured between electrodes 415 and 440, and changes in this measurement will be due at least in part to clitoral tumescence change. The measurements taken by the electrodes according to the invention, such as electrodes 415, 440, can reflect engorgement/blood-flow changes in the labia, vagina, clitoris and/or other areas.

Insertion unit 420 optionally includes a vaginal pressure measurement device. Tip portion 425 of insertion unit 420 is preferably of constructed of a flexible material, e.g. a rubber- or plastic-type material in the manner of a child's pacifier, and includes hollowed-out portion 455 filled with air, saline or other fluid. An inflatable balloon-type construction is contemplated. Changes in external pressure on insertion unit 420, which directly reflect changes in vaginal pressure, cause corresponding pressure changes within hollowed-out portion 455. Pressure transducer 460, which can be screwed or otherwise inserted into base member 430, senses the pressure changes within hollowed-out portion 455. Thus, this embodiment of the invention achieves accurate vaginal pressure measurements.

Electrodes 405, 410, 415, 440 and 445 all are operably coupled to control and/or monitoring unit 465, shown in FIG. 16, by respective leads 405A, 410A, 415A, 440A and 445A. Likewise, lead 460A connects pressure transducer 460 to the control unit. To reduce size and weight, the primary function of unit 465 preferably is data collection and storage for later downloading to a computer or other associated device, in a manner previously described. Alternatively, processing electronics can be incorporated into unit 465 itself, although this likely would increase the unit's size, weight, power requirements, etc. Unit 465 can be strapped to the leg or other portion of the patient's body, according to one embodiment. In the case of larger electronics, desktop-type, laptop-type and other computing devices can be used. Diurnal and nocturnal monitoring/measurements are contemplated.

Figure 17:
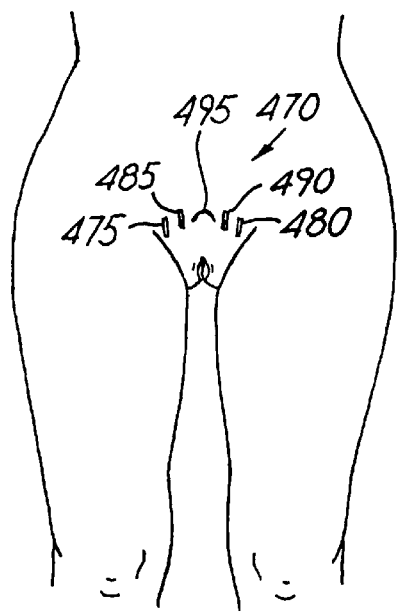
FIG. 17 shows an alternative measurement device for determining clitoral engorgement, according to an embodiment of the invention.

Of course, other electrode configurations and placements are contemplated according to embodiments of the invention. FIG. 17, for example, illustrates the electrodes of a clitoral vasocongestion sensing device 470 in place on a female patient. Leads, electronics and other previously described features are omitted from FIG. 17, for clarity of illustration. According to this embodiment, electrodes 475, 480 are the source and sink for device 470, and electrodes 485, 490 are the voltage-sensing electrodes. Vasocongestion in clitoris 495 can be determined, in accordance with the theories discussed above.

Combination Systems

Figure 18:
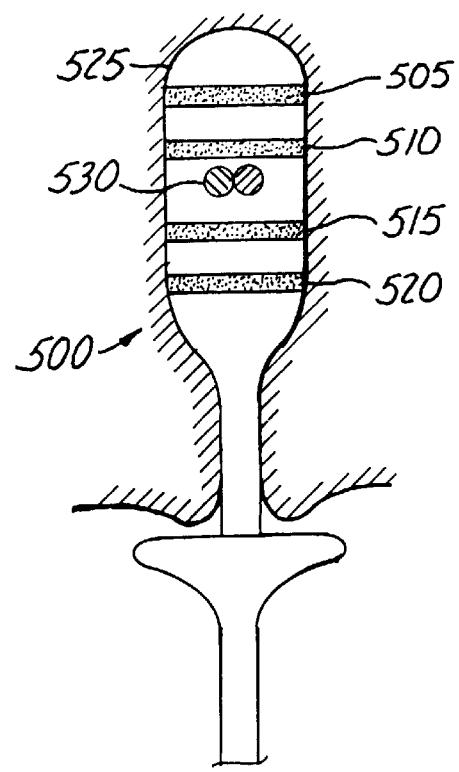
FIGS. 18–19 show combination measurement probes, according to embodiments of the invention.
Figure 19:
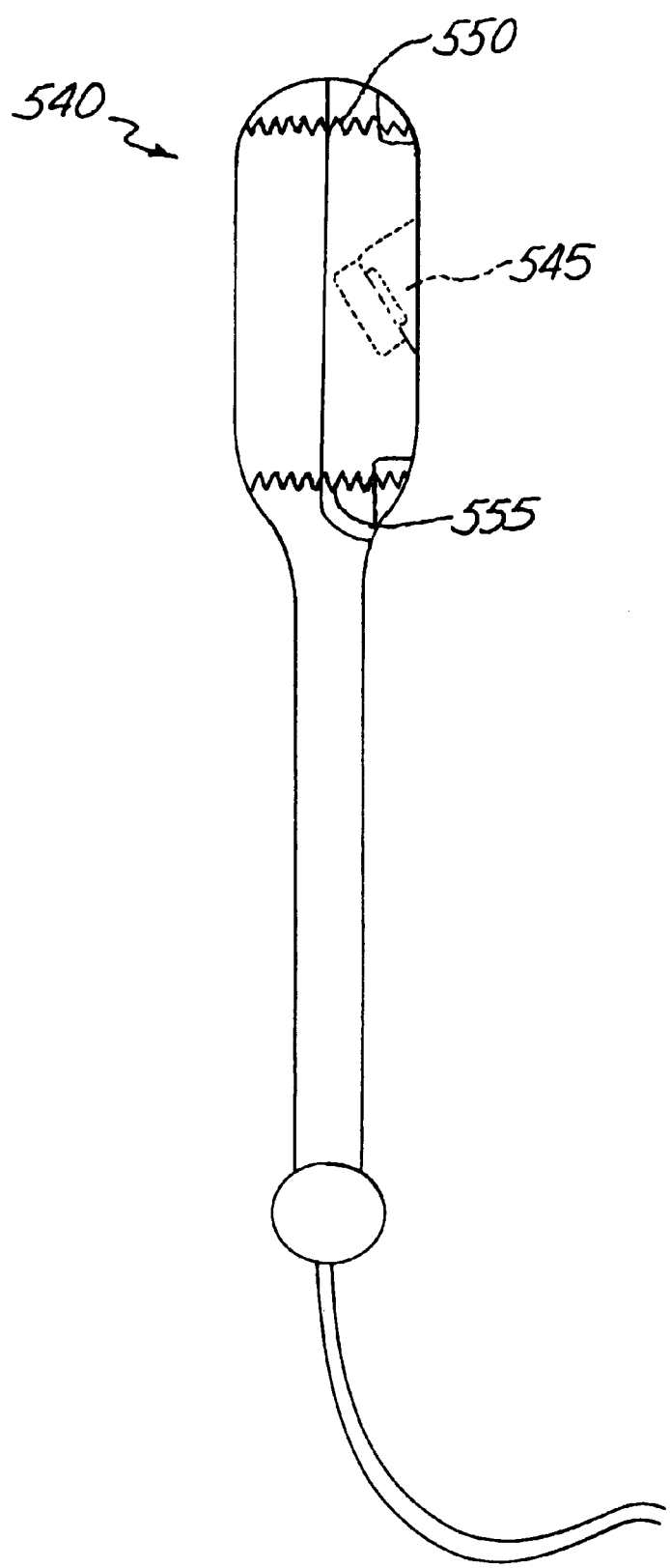

The above-described devices and corresponding methods can be combined to form a variety of combination arousal monitoring systems, according to embodiments of the invention. For example, as shown in FIG. 18, monitoring device 500 includes multiple bioimpedance electrodes, in the illustrated case four such electrodes 505, 510, 515, 520, for use as described above. Alternatively, a number of other variables can be measured using one or more such electrodes or alternative sensing devices, such as pH, fluid/moisture content, conductivity, temperature, oxygenation, etc. Tip end 525 of device 500 can include one or more oximeter probes, ultrasound transducers, and/or other sensing devices 530 as described above, for example. With such devices, differences in blood flow, fluid flow, or other parameters can be monitored along the length of the vagina to determine problem areas caused by disease or trauma, for example. Similarly, FIG. 19 shows ultrasound transducer 545, useable for example in the manner described in PCT Publication No. WO 98/06333, discussed above, in combination with two sensing electrodes 550, 555, also useable as previously described.

In fact, any of the particular systems and methods described herein can be used with any one or multiple other particular systems. To list a few more examples, the "pacifier-type" unit 420 of FIG. 15 can be used with four electrodes and/or can be combined with the four-electrode system of FIG. 17. The clitoral monitoring devices of FIGS. 1 and 1A can be used with any of the oximetry devices described herein. This disclosure will enable one of ordinary skill to make and use various other combinations and permutations of the individual devices discussed herein.

Cardiac Cycle Information

Cardiac cycle information can be used to analyze the data measured and recorded by the devices hereindescribed. This can provide significant advantages in confirming that arousal is actually occurring. According to embodiments of the invention, increases in cardiac cycle amplitude can have significance in the analysis of data generated and recorded according to embodiments of the invention. For example, according to embodiments of the invention, an impedance waveform is generated using plural electrodes placed in a manner as described above A cardiac signature is detected in the impedance waveform. The cardiac signature is used to detect and appropriately signal arousal events, readily allowing non-arousal events/artifacts to be distinguished.

Blood courses into the vaginal and/or clitoral area during an arousal event in a manner associated with the cardiac cycle. Instead of entering continuously, the blood enters in a pulsatile manner. Given the relationship between blood volume and impedance, embodiments of the invention detect a pulsatile component of the impedance waveform and use its existence to indicate the presence of an arousal event. This pulsatile component of impedance, or "cardiac signature," is quite small compared to the magnitude of the impedance, on the order of one one-thousandth of it, but it can be detected and used to signal an event. The cardiac signature can be detected by e.g. applying the impedance waveform to a 0.5 Hz to 10 Hz band-pass filter, which removes the baseline (DC component) and allows the impedance waveform to be scaled up for better visibility.

Cardiac signatures that indicate arousal events can be detected e.g. by computer software that recognizes the periodic nature, i.e. the frequency content, of the cardiac signature. A fundamental (e.g., the lowest frequency of a periodically varying quantity) is detected, the frequency of which is proportional to the reciprocal of the period of the waveform. According to one embodiment, the software looks for the existence of a fundamental and a corresponding, relatively small spectral bandwidth as indicative of pulsatile activity associated with an arousal event. Other embodiments can also consider second and potentially third harmonics in performing the analysis.

Attention is directed to commonly assigned PCT Publication No. WO 98/42255, referenced above, which includes a more detailed discussion of cardiac cycle information and its correlation to volumetric and other measurements.

Conclusion

While the invention has been described with respect to particular embodiments, the invention is by no means limited to the specific embodiments illustrated and described herein. For example, measuring devices according to the invention can include multiple transducers and/or electrodes spaced circumferentially and/or linearly from each other at a distal end of or otherwise along the probe, with or without independently rotatable housing portions, for simultaneously measuring and monitoring blood flow in both the left and right vaginal arteries, vaginal-wall and/or clitoral blood flow, and/or the other parameters and variables described above. A photoplethysmographic probe can be combined with bioimpedance or other-type electrodes mounted thereon or used in association therewith. Audio, visual, tactile or other types of sensory feedback can be used with any of the above-described embodiments.

Generally speaking, all of the above-described embodiments can use a condom, disposable sheath, probe cover or other protective membrane to promote cleanliness and provide the resulting medical and psychological advantages associated therewith. For example, the ECLIPSE probe cover, available from Parker Laboratories, Fairfield, New Jersey, can be used. Embodiments of the invention can also be disposable, for single-use situations, or sterilizable (or otherwise adequately cleanable) for multiple uses.

According to embodiments of the invention, the sensing elements and control electronics generate and/or receive various types of data signals, representing e.g. blood parameters, blood velocities, clitoral or cavernosal-artery or other diameters, blood volumes and/or pulse amplitudes, or any of a host of other possible variables.

All of the above-described embodiments can lend themselves well to overnight arousal-event monitoring, either at home or away from home, for diagnosis of vasculogenic impairment or other problems. Continuous monitoring over extended periods of time is contemplated, with simultaneous or subsequent data downloading and/or analysis. Embodiments of the invention provide objective, quantifiable measures of multiple physiological variables associated with female arousal, in a manner heretofore unseen in the prior art. Data regarding each of those variables can be displayed or analyzed individually, separately or in any combination (e.g. graphical, numerical or other data representing $SpO_2$, VBV, VPA, and, optionally, pH, can all be displayed together, individually, or in any combination). Embodiments of the invention also can be used to measure the effects of medicinal therapies, e.g. hormonal therapies or other therapies associated with drugs for addressing female sexual dysfunction. The quantifiable results achieved according to the invention thus can be used to titrate proper dosages, for example, to deliver the minimum effective dose and thus reduce undesirable side effects. Various other modifications and changes are readily discernable from the specification and will be apparent to those of ordinary skill.

What is claimed is:

1. A measurement device, comprising:
   at least one sensing element constructed for placement in proximity to at least one female anatomical structure, the at least one female anatomical structure being selected from the group consisting of the vagina and the clitoris, the at least one sensing element being constructed to produce first data signals;
   a housing constructed for supporting the at least one sensing element in a substantially fixed relationship with respect to at least one blood vessel within the female anatomical structure, the at least one blood vessel including the clitoral cavernosal artery, such that the first data signals are related to a blood parameter associated with the clitoral cavernosal artery; and
   control electronics operably coupled with the at least one sensing element to receive the first data signals.

2. The device of claim 1, wherein the at least one sensing element comprises an ultrasound transducer.

3. The device of claim 2, further comprising an ultrasound standoff in close proximity to the ultrasound transducer, the ultrasound standoff being constructed for passage of ultrasound energy, the ultrasound standoff further being constructed for application to the female clitoris.

4. The device of claim 2, wherein the control electronics process the first data signals to generate second data signals representing clitoral cavernosal artery blood velocity.

5. The device of claim 4, wherein the control electronics additionally process the first data signals to generate third data signals representing clitoral diameter or cavernosal artery diameter.

6. The device of claim 2, wherein the housing comprises an elongate shaft constructed for insertion into the vagina, the ultrasound transducer being disposed at a distal end of the elongate shaft.

7. The device of claim 6, wherein the at least one sensing element comprises a plurality of ultrasound transducers.

8. The device of claim 7, wherein the plurality of ultrasound transducers are disposed on the elongate shaft so as to aim toward both vaginal arteries of the female.

9. The device of claim 8, wherein the plurality of ultrasound transducers are supported for movement relative to the elongate shaft substantially about a longitudinal axis of the elongate shaft.

10. The device of claim 7, further comprising an adjustable housing portion constructed for supporting one of the plurality of ultrasound transducers, the adjustable housing portion being coupled with the elongate shaft to adjust the distance between the elongate shaft and the ultrasound transducer supported by the adjustable housing portion.

11. The device of claim 10, wherein the adjustable housing portion is pivotally connected to the elongate shaft.

12. The device of claim 10, wherein the plurality of ultrasound transducers comprises three ultrasound transducers, a first of the three ultrasound transducers disposed for taking measurements from one vaginal artery, a second of the three ultrasound transducers disposed for taking measurements from the second vaginal artery, and a third of three ultrasound transducers disposed for taking measurements from the clitoral cavernosal artery.

13. The device of claim 1, wherein the control electronics comprise a memory for storing data based on the first data signals.

14. The device of claim 1, further comprising a display constructed to continuously receive data signals from the control electronics for monitoring sexual arousal of the female.

15. The device of claim 1, wherein the at least one sensing element comprises a plurality of electrodes, further wherein the control electronics process the first data signals to produce second data signals that represent blood-volume changes in the female vaginal wall, the labia, and/or the clitoris.

16. The device of claim 15, wherein at least two of the plurality of electrodes are both secured to one adhesive strip.

17. The device of claim 15, further comprising an insertion mechanism on which at least two of the plurality of electrodes are disposed, wherein the plurality of electrodes additionally comprise at least two subumbilical electrodes; further wherein the first data signals are generated when the insertion mechanism is inserted into the vagina and when the at least two subumbilical electrodes are positioned subumbilically on the patient.

18. The device of claim 15, wherein the housing comprises a vaginal-pressure measurement device for generating vaginal-pressure data signals.

19. The device of claim 18, wherein the vaginal-pressure measurement device comprises a flexible outer material defining a hollowed-out inner portion filled with a fluid.

20. The device of claim 15, wherein the control electronics detect a cardiac signature in an impedance waveform derived at least in part from the first data signals, the control electronics generating third data signals representing the cardiac signature data.

21. A measurement device, comprising:
at least one oximeter probe constructed for placement in proximity to the vaginal wall of a female subject, the at least one oximeter probe generating first data signals;
a housing constructed for supporting the at least one oximeter probe in close association with the vaginal wall; and
control electronics for receiving the first data signals and generating second data signals representing at least one of vaginal blood volume and vaginal pulse amplitude.

22. The device of claim 21, wherein the housing comprises a probe-supporting portion and a neck portion connected thereto, the probe-supporting portion being of wider dimension that the neck portion.

23. The device of claim 21, wherein the control electronics generate third data signals representing oxygenation level of the hemoglobin in the capillaries of the vaginal wall, the device further comprising a display for receiving the third data signals and displaying the oxygenation level as an $SpO_2$ variable.

24. The device of claim 21, further comprising at least one photoplethysmographic probe supported by the housing and operably coupled with the control electronics.

25. The device of claim 24, further comprising an audio feedback device for receiving the second data signals, the audio feedback device generating an audible sound that is a function of the vaginal pulse amplitude.

26. The device of claim 21, further comprising at least one electrode supported by the housing for generating data signals related to a vaginal parameter, the control electronics receiving the vaginal-parameter data signals.

27. The device of claim 26, wherein the vaginal parameter is selected from the group consisting of pH, bioimpedance, and temperature.

28. The device of claim 21, further comprising a pressure balloon operably coupled with a pressure source, the pressure balloon being disposed so as to urge the oximeter probe toward the vaginal wall with a desired pressure.

29. The device of claim 28, further comprising an automatic pressure-regulation mechanism, operably coupled with the pressure balloon and the control electronics, for automatically maintaining the contact pressure between the vaginal wall and the oximeter probe.

30. A measurement device, comprising:
sensing means for producing first data signals, the sensing means being constructed for placement in proximity to at least one female anatomical structure, the at least one female anatomical structure being selected from the group consisting of the vagina and the clitoris;
means for supporting the sensing means in a substantially fixed relationship with respect to at least one blood vessel within the female anatomical structure, such that the first data signals are related to a blood parameter associated with the at least one blood vessel, the at least one blood vessel including the clitoral cavernosal artery; and
means, operably coupled with the sensing means, for receiving the first data signals.

31. A measurement device, comprising:
at least one sensing element constructed for placement in proximity to at least one female anatomical structure, the at least one female anatomical structure being selected from the group consisting of the vagina and the clitoris, the at least one sensing element being constructed to produce first data signals;
a housing constructed for supporting the at least one sensing element in a substantially fixed relationship with respect to at least one blood vessel within the female anatomical structure, the at least one blood vessel being selected from the group consisting of the vaginal artery and the clitoral cavernosal artery, such that the first data signals are related to a blood parameter associated with the at least one blood vessel; and
control electronics operably coupled with the at least one sensing element to receive the first data signals;
wherein the at least one sensing element comprises an ultrasound transducer;
further wherein the control electronics process the first data signals to generate second data signals representing clitoral cavernosal artery blood velocity.

32. A measurement device, comprising:
at least one sensing element constructed for placement in proximity to at least one female anatomical structure, the at least one female anatomical structure being selected from the group consisting of the vagina and the clitoris, the at least one sensing element being constructed to produce first data signals, wherein the at least one sensing element comprises a plurality of ultrasound transducers;
a housing constructed for supporting the at least one sensing element in a substantially fixed relationship with respect to at least one blood vessel within the female anatomical structure, the at least one blood vessel being selected from the group consisting of the vaginal artery and the clitoral cavernosal artery, such that the first data signals are related to a blood parameter associated with the at least one blood vessel, wherein the housing comprises an elongate shaft constructed for insertion into the vagina, at least one of the plurality of ultrasound transducers being disposed at a distal end of the elongate shaft;
control electronics operably coupled with the at least one sensing element to receive the first data signals; and
an adjustable housing portion constructed for supporting one of the plurality of ultrasound transducers, the adjustable housing portion being coupled with the elongate shaft to adjust the distance between the elongate shaft and the ultrasound transducer supported by the adjustable housing portion;
wherein the plurality of ultrasound transducers comprises three ultrasound transducers, a first of the three ultrasound transducers disposed for taking measurements from one vaginal artery, a second of the three ultrasound transducers disposed for taking measurements from the second vaginal artery, and a third of three ultrasound transducers disposed for taking measurements from the clitoral cavernosal artery.

33. A measurement device, comprising:
at least one sensing element constructed for placement in proximity to at least one female anatomical structure, the at least one female anatomical structure being selected from the group consisting of the vagina and the clitoris, the at least one sensing element being constructed to produce first data signals;
a housing constructed for supporting the at least one sensing element in a substantially fixed relationship with respect to at least one blood vessel within the female anatomical structure, the at least one blood vessel being selected from the group consisting of the vaginal artery and the clitoral cavernosal artery, such that the first data signals are related to a blood parameter associated with the at least one blood vessel; and
control electronics operably coupled with the at least one sensing element to receive the first data signals;
wherein the at least one sensing element comprises a plurality of electrodes, further wherein the control electronics process the first data signals to produce second data signals that represent blood-volume changes in the female vaginal wall, the labia, and/or the clitoris.

34. A measurement device, comprising:
at least one oximeter probe constructed for placement in proximity to the vaginal wall of a female subject, the at least one oximeter probe generating first data signals;
a housing constructed for supporting the at least one oximeter probe in close association with the vaginal wall;
control electronics for receiving the first data signals and generating second data signals representing oxygenation level of the hemoglobin in the capillaries of the vaginal wall; and
at least one photoplethysmographic probe supported by the housing and operably coupled with the control electronics, the control electronics generating third data signals representing at least one of vaginal blood volume and vaginal pulse amplitude.

35. A measurement device, comprising:
at least one oximeter probe constructed for placement in proximity to the vaginal wall of a female subject, the at least one oximeter probe generating first data signals;
a housing constructed for supporting the at least one oximeter probe in close association with the vaginal wall;
control electronics for receiving the first data signals and generating second data signals representing oxygenation level of the hemoglobin in the capillaries of the vaginal wall; and
at least one electrode supported by the housing for generating data signals related to a vaginal parameter, the control electronics receiving the vaginal-parameter data signals.

36. A measurement device, comprising:
at least one oximeter probe constructed for placement in proximity to the vaginal wall of a female subject, the at least one oximeter probe generating first data signals;
a housing constructed for supporting the at least one oximeter probe in close association with the vaginal wall;
control electronics for receiving the first data signals and generating second data signals representing oxygenation level of the hemoglobin in the capillaries of the vaginal wall;
a pressure balloon operably coupled with a pressure source, the pressure balloon being disposed so as to urge the oximeter probe toward the vaginal wall with a desired pressure; and
an automatic pressure-regulation mechanism, operably coupled with the pressure balloon and the control electronics, for automatically maintaining the contact pressure between the vaginal wall and the oximeter probe.

* * * * *